United States Patent [19]

Anton et al.

[11] Patent Number: 5,593,871
[45] Date of Patent: Jan. 14, 1997

[54] PROCESS FOR THE PREPARATION OF ENANTIOMETRIC 2-ALKANOIC ACID AMIDES FROM NITRILES

[75] Inventors: David L. Anton, Wilmington, Del.; Robert D. Fallon, Elkton, Md.; Barry Stieglitz, Overbrook Hills, Pa.; Vincent G. Witterholt, Wilmington, Del.

[73] Assignee: E. I. Du Pont de Nemours and Company, Wilmington, Del.

[21] Appl. No.: 388,921

[22] Filed: Feb. 15, 1995

Related U.S. Application Data

[63] Continuation-in-part of Ser. No. 30,015, Mar. 22, 1993, abandoned, which is a continuation-in-part of Ser. No. 585,554, Sep. 20, 1990, abandoned.

[51] Int. Cl.$^6$ .............. C12P 13/02; C12P 17/18; C12P 17/14; C12P 17/10
[52] U.S. Cl. .............. 435/129; 435/119; 435/120; 435/121; 435/122; 435/280
[58] Field of Search .............. 435/129, 280, 435/119–122

[56] References Cited

U.S. PATENT DOCUMENTS

| | | | |
|---|---|---|---|
| 4,366,250 | 12/1982 | Jallageas et al. | 435/280 |
| 4,629,700 | 12/1986 | Prevatt et al. | 435/227 |
| 4,637,982 | 1/1987 | Yamada et al. | 435/129 |
| 4,661,456 | 4/1987 | Yamada et al. | 435/227 |
| 4,661,457 | 4/1987 | Yamada et al. | 435/227 |
| 4,705,752 | 11/1987 | Boesten et al. | 435/227 |
| 4,800,162 | 1/1989 | Matson | 435/280 |
| 4,880,737 | 11/1989 | Kerhoffs et al. | 435/227 |
| 4,880,739 | 11/1989 | Yamada et al. | 435/42 |
| 4,900,672 | 2/1990 | Yamada et al. | 435/227 |
| 5,179,014 | 1/1993 | Watanabe et al. | 435/129 |
| 5,200,331 | 4/1993 | Kawakami et al. | 435/129 |
| 5,283,193 | 2/1994 | Yamamoto et al. | 435/280 |

FOREIGN PATENT DOCUMENTS

| | | |
|---|---|---|
| 0326482 | 8/1989 | European Pat. Off. |
| 0330529 | 8/1989 | European Pat. Off. |
| 0348901 | 1/1990 | European Pat. Off. |
| 0356912 | 3/1990 | European Pat. Off. |
| WO86/07386 | 12/1986 | WIPO |

*Primary Examiner*—Irene Marx
*Assistant Examiner*—S. Saucier

[57] ABSTRACT

This invention relates to the enantioselective biologically-catalyzed hydrolysis of certain racemic nitriles to the corresponding R- or S-amides, chemically or biologically-catalyzed hydrolysis of the amides to the corresponding R- or S-acids in a batch process or in a continuous process that employs racemization and recycling of enantiomeric nitrile intermediates, the racemic nitriles being selected from the group, $A—C(R^1)(R^2)CN$, wherein A, $R^1$ and $R^2$ are as defined in the text, as well as certain biological materials employed to catalyze the process.

10 Claims, No Drawings

PROCESS FOR THE PREPARATION OF ENANTIOMETRIC 2-ALKANOIC ACID AMIDES FROM NITRILES

CROSS REFERENCE TO RELATED APPLICATION

This application is a continuation-in-part of U.S. Ser. No. 08/030,015 filed Mar. 22, 1993, which in turn is a continuation-in-part of U.S. Ser. No. 07/585,554 filed Sep. 20, 1990 both now abandoned.

FIELD OF THE INVENTION

Enantiospecific biologically-catalyzed hydrolysis of nitriles to the corresponding enantiomers of 2-alkanoic acids via enantiomeric amide intermediates.

STATE OF THE ART

Products intended for use in biological systems must often be synthesized in a particular enantiomeric form due to preferences that correlate with the "handedness" (i.e., optical rotation) of the molecule. For example, only the S-form of the widely prescribed anti-inflamatory Naproxen (2-(6-methoxy-2-naphthyl)-propionic acid) is clinically effective; the R-form is toxic [R. N. Brogden et al., Drugs 18:241–277(1979)]. Therefore, the drug must be supplied such that the S-enantiomer, and not the R-enantiomer, is highly enriched in the final product. A similar situation exists for many other pharmaceutical and agricultural chemicals. However, the synthesis chemist is often faced with a difficult problem because most chemical catalysts do not discriminate by optical form. In fact, it is very difficult to synthesize a single enantiomer. Moreover, because enantiomers, by definition, have identical physical properties and differ only in the direction that they rotate plane polarized light, separation of individual enantiomers from a mixture of S- and R-enantiomers is difficult.

Within the family of nitrile hydrolyzing enzymes, two broad classes are generally recognized. The first includes the nitrile hydratases (NHase) which bring about the addition of one molecule of water to the nitrile, resulting in the formation of an amide product:

Reaction 1   R—CN+H$_2$O→RC(O)NH$_2$

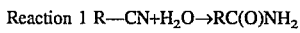

The second group includes the nitrilases which bring about the addition of two molecules of water to the nitrile resulting in formation of an acid product plus ammonia:

Reaction 2   R—CN+2H$_2$O→RC(O)OH+NH$_3$

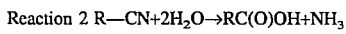

A third class of enzymes, amidases, convert the product of Reaction 1 to the acid product plus ammonia:

Reaction 3   RC(O)NH$_2$→RC(O)OH+NH$_3$

Recent reviews [e.g., Wyatt, J M and Linton E A, The industrial potential of microbial nitrile biochemistry, (1988)] disclose a diversity of amenable substrates for nitrile hydrolyzing enzymes found in bacterial genera such as Rhodococcus, Pseudomonas, Alcaligenes, Arthrobacter, Bacillus, Bacteridium, Brevibacterium, Corynebacterium, and Micrococcus. Numerous patents and publications describe conversion of aliphatic nitriles and their derivatives to corresponding amides and acids.

WO 86/07386 discloses a process for preparing amino acids or amino acid amides from an enantiomeric mixture of the corresponding amino nitrile with an enantioselective nitrilase and subsequent recovery of the resulting optically-active amino acid or amino amide. This publication does not suggest the instant invention because it utilizes different microorganisms and the hydrolyses described are stereoselective, not stereospecific.

EPA 326,482 discloses the stereospecific preparation of aryl-2-alkanoic acids such as 2-(4-chlorophenyl)-3-methyl-butyric acid by microbial hydrolysis of the corresponding racemic amide. Microorganisms disclosed in EPA 326,482 include members of Brevibacterium and Corynebacterium. The process was performed batchwise without organic solvent, and the enzymatically-active material was discarded after being used once. Data in the examples of EPA 326,482 indicate that 35 to 60% of the S-amide remained unconverted. The enantiomeric excess of the S-acid produced was 92 to 97%.

U.S. Pat. No. 4,366,250 discloses a process for preparing L-amino acids from the corresponding racemic amino nitrile with bacteria having a general nitrile hydratase and a L-stereospecific amidase. Microorganisms are chosen from Bacillus, Bacteridium, Micrococcus and Brevibacterium.

EPA 356,912 discloses preparation of optically-active 2-substituted carboxylic acids by hydrolysis of the corresponding racemic nitrile in the presence of a microorganism or enzyme. The microorganisms employed do not suggest those found herein to convert nitriles to the amide precursors of the acids.

EPA 348,901 discloses a process for producing an optically-active α-substituted organic acid of Formula ii by treating a racemic α-substituted nitrile or amide of Formula i with a microorganism selected from the group Alcaligenes, Pseudomonas, Rhodopseudomonas, Corynebacterium, Acinetobacter, Bacillus, Mycobacterium, Rhodococcus and Candida;

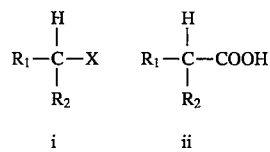

wherein:

R$_1$ and R$_2$ each represent halogen; hydroxy; substituted or unsubstituted alkyl, cycloalkyl, alkoxy, aryl, aryloxy or heterocycle; provided that R$_1$ and R$_2$ are different; and X is a nitrile or amido group. See also, Yamamoto et al., Appl. Envir. Microbiol., 56(10), 3125–9, 1990.

EPA 330,529 discloses a process employing Brevibacterium and Corynebacterium for the preparation of the S-enantiomers of aryl-2-propionic acids of Formula iii

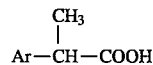

from the corresponding racemic aryl-2-propionamide wherein Ar represents a substituted or unsubstituted monocyclic or polycyclic aromatic or heteroaromatic radical.

U.S. Pat. No. 4,800,162 discloses the resolution of racemic mixtures of optically-active compounds such as esters, amides, carboxylic acids, alcohols and amines using multiphase and extractive enzyme membranes.

The instant invention comprises the use of particular nitrile hydratase enzymes that preferentially hydrolyze only one enatiomer of an R,S mixture of nitriles. These enzymes mediate the single-step conversion of a racemic nitrile mixture into a mixture consisting of the nitrile of one enantiomeric form and an amide of the opposite enantiomeric form. The resulting amide and nitrile are easily separated from one another due to their distinct chemical and physical properties.

The instant invention represents a significant improvement over the prior art, producing the enatiomerically enriched amide in a single step from the racemic nitrile via a nitrile hydratase enzyme, leaving the enatiomerically enriched nitrile by-product intact. In contrast, the processes described in the prior art produce the enatiomerically enriched acid products via two-step processes involving both nitrile hydratase and amidase enzymes, leaving the enantiomerically enriched amide by-products intact. Amide products produced by nitrile hydratases in a single step (e.g., acrylamide) have been described previously (e.g., U.S. Pat. No. 4,637,982); however this art is silent on production of enantiomerically enriched products. In addition, as described in Table 1, only particular enzymes disclosed in the instant process are useful for enantiomeric enrichment of the amide product.

SUMMARY OF THE INVENTION

This invention concerns certain individual and combined steps in a biologically-catalyzed method for converting a racemic alkyl nitrile to the corresponding R- or S-alkanoic acid through an intermediate amide. The starting nitrile is:

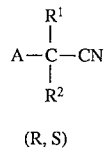

(R, S)

wherein:
A is selected from the group consisting of:

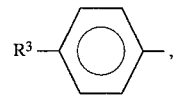  A-1

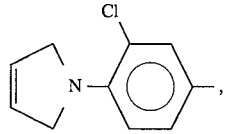  A-2

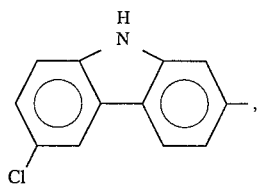  A-3

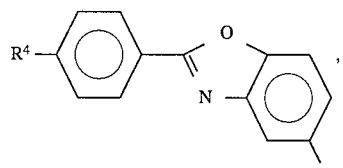  A-4

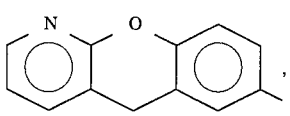  A-5

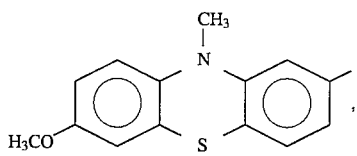  A-6

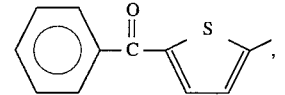  A-7

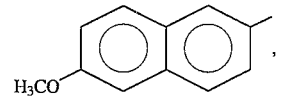  A-8

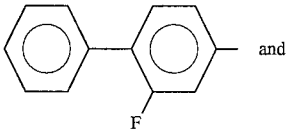  A-9

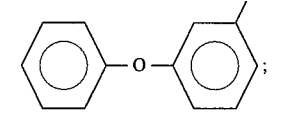  A-10

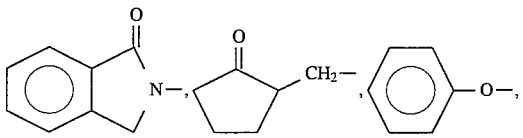  A-11

$R^1$ is $C_1$–$C_4$ alkyl;
$R^2$ is H or OH;
$R^3$ is H, Cl, $OCF_2H$, $(CH_3)_2CHCH_2$, $H_2C=C(CH_3)CH_2NH$, $R^4$ is Cl or F.

Preferred values of A are A-1, A-5, A-9, A-10 and A-11. Preferred values of A-1 are those wherein $R^3$ is selected from the group Cl, $(CH_3)_2CHCH_2$,

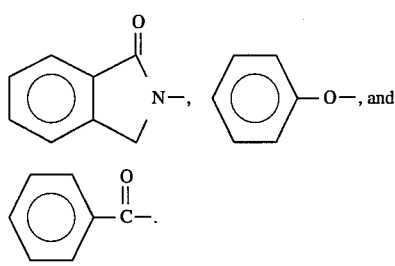

Preferred values for $R^1$ are $CH_3$ and $CH(CH_3)_2$.

Preparation of the amide, in Step i of the method of this invention, comprises contacting I with a biological material that stereospecifically converts the R,S mixture of nitriles of Formula I to either the R- or S-amide wherein said R- or S-amide is substantially free of the opposite enantiomer. Resolution of the mixed R- and S-enantiomer of a nitrile of Formula I to resolved amide is followed by conversion to the corresponding acid of Formula II by Step ii of the method of this invention:

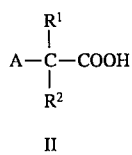

II

The amide intermediate is $A-C(R^1)(R^2)-CONH_2$. This invention also concerns the racemization (Step iii) and subsequent recycle of unconverted R- or S-nitrile, when $R^2$ is H, from Step ii back to the original reactor in a continuous process. In the continuous process, the racemic alkyl nitrile starting reactant is contacted with biological material containing or comprising nitrile hydratase and amidase enzymes at the same time or consecutively to proceed first to the amide (Step i) and then to the acid (Step ii). Alkyl acid is continually removed and by-product R- or S-alkyl nitrile in which $R^2$ is H is racemized and recycled in a continuous process in which it is combined with additional alkyl nitrile and contacted with enzyme(s) to form the alkyl amide and then the acid.

This invention is particularly characterized by the biological material (a microorganism or variant or mutant thereof, or an enzyme) employed in Step i and by the combination of biological catalysis (Step i) with mineral acid hydrolysis (Step ii) or known amidase enzymes (Step ii). The nitrile racemization is characterized by the use of a strongly basic ion exchange resin in the absence of any substantial amount of water and most preferably in the presence of a nonaqueous solvent such as methanol, ethanol, toluene, dioxane and the like. To simplify the description of this invention, the method will be explained with reference to the enzymes found to be useful.

Preferred Step i enzymes comprise those found in the following microorganisms: *Pseudomonas spp.*, e.g., *putida, aureofaciens, Moraxella spp.*, Serratia, e.g., *Serratia liquefaciens*. These enzymes can be isolated or biosynthesized and used as such but it is usually more convenient to employ the appropriate microorganism(s).

In this method for hydrating and converting an R,S mixture of nitrile to the corresponding R- or S- enantiomeric acid, Step i is accomplished by the action of a stereospecific nitrile hydratase enzyme originating in a microorganism which is obtained by culturing the microorganism in the presence of a medium suitable for production of the stereospecific nitrile hydratase. This medium may include nitriles or amides as enzyme inducers or in the case of *Pseudomonas putida* 5B-MGN-2p, which produces the enzyme constitutively in the absence of an inducer, need include only an appropriate source of nitrogen for growth (e.g., ammonium chloride). The nitrile hydratase thus obtained is added to act upon either R- or S-nitriles to yield the corresponding R- or S-amides. In Step ii, the R- or S-amide is hydrolyzed by mineral acid or amidase enzyme to the corresponding R- or S-acid.

This two-step method results in a mixture of an R- or S-acid and an S- or R-nitrile, respectively. Chiral nitrile and acid are first separated by neutralization and solvent extraction. Then, the chiral nitrile is racemized into a mixture of R,S nitrile which can again be hydrolyzed stereospecifically into R- or S-amide by the action of the stereospecific nitrile hydratase described in Step i.

One method for inducing the nitrile hydratase to act upon the nitrile is to collect the enzyme from the microorganism that produces it and use the enzyme as an enzyme preparation in a biologically-recognized manner.

This invention also concerns a biological material located in or derived from *Pseudomonas sp.* 3L-G-1-5-1a, *Pseudomonas sp.* 2G-8-5-1a, *P. putida* 5B-MGN-2p and *P. aureofaciens* MOB C2-1, or a variant or mutant thereof, which material stereospecifically converts a racemic nitrile to the corresponding enantiomeric R- or S-amide.

DETAILS OF THE INVENTION

In the context of the present disclosure, the terms "stereospecific reaction" or "stereospecific nitrile hydratase" are defined by the enantiomeric ratio (E) for the R- and S-enantiomers:

$$E_{S\text{-}product}=(S/hr)/(R/hr)=S/R$$

wherein S=the weight of the S-enantiomer product and R=the weight of the R-enantiomer product. E is analogous to the numerator in the term of art "enantiomeric excess" (ee), wherein $$ee_{S\text{-}product}=(S-R)/(S+R).$$

E corresponds to the ratio of the rate of reaction of the two enantiomers. When E is high, i.e., greater than 7, the reaction is stereospecific and when E is less than 7, the reaction is stereoselective. Preferred reactions are those wherein E is above 8.5 and most preferred reactions are those wherein E is 10 or above.

Abbreviations
CPIN—2-(4-chlorophenyl)-3-methylbutyronitrile
CPIAm—2-(4-chlorophenyl)-3-methylbutyramide
CPIA—2-(4-chlorophenyl)-3-methylbutyric acid
IBCN—2-(4-isobutylphenyl)-propionitrile
IBAm—2-(4-isobutylphenyl)-propionamide
IBAC—2-(4-isobutylphenyl)-propionic acid (ibuprofen)
NPCN—2-(6-methoxy-2-naphthyl)-propionitrile
NPAm—2-(6-methoxy-2-naphthyl)-propionamide
NPAC—2-(6-methoxy-2-naphthyl)-propionic acid
HPLC—High-Performance Liquid Chromatography
GC—Gas Chromatography DMSO—Dimethylsulfoxide.

Step i

The microorganisms used in the present invention belong to the genera Pseudomonas, Moraxella, and Serratia. Representative strains include *P. putida*, 5B-MGN-2P; *Moraxella sp.*, 3L-A-1-5-1a-1; *P. putida*, 13-5S-ACN-2a; *Pseudomonas sp.*, 3L-G-1-5-1a; and *Serratia liquefaciens*, MOB IM/N3. These strains were deposited under the terms of the Budapest Treaty at NRRL (Northern Regional Research Center, U.S. Department of Agriculture, 1815 North University St., Peoria, Ill.) and bear the following accession numbers:

| Organism | Deposit Number | Deposit Date |
|---|---|---|
| *P. putida* 5B-MGN-2P | NRRL-B-18668 | July 6, 1990 |
| Moraxella sp. 3L-A-1-5-1a-1 | NRRL-B-18671 | July 6, 1990 |
| *P. putida* 13-5S-ACN-2a | NRRL-B-18669 | July 6, 1990 |
| Pseudomonas sp. 3L-G-1-5-1a | NRRL-B-18670 | July 6, 1990 |
| *Serratia liquifaciens* MOB IM/N3 | NRRL-B-18821 | May 10, 1991 |
| *P. putida* 2D-11-5-1b | NRRL-B-18820 | May 10, 1991 |
| Pseudomonas sp. 2D-11-5-1c | NRRL-B-18819 | October 17, 1991 |
| Pseudomonas sp. 2G-8-5-1a | NRRL-B-18833 | October 29, 1991 |
| *P. aureofaciens* MOB C2-1 | NRRL-B-18834 | June 5, 1991 |

The above strains were isolated from soil collected in Orange, Tex. Standard enrichment procedures were used with the following modified medium (PR Basal Medium).

| PR Basal Medium | |
|---|---|
| | g/L |
| $KH_2PO_4$ | 8.85 |
| Sodium citrate | 0.225 |
| $MgSO_4.7H_2O$ | 0.5 |
| $FeSO_4.7H_2O$ | 0.05 |
| $FeCl_2.4H_2O$ | 0.0015 |
| $CoCl_2.6H_2O$ | 0.0002 |
| $MnCl_2.4H_2O$ | 0.0001 |
| $ZnCl_2$ | 0.00007 |
| $H_3BO_3$ | 0.000062 |
| $NaMoO_4.2H_2O$ | 0.000036 |
| $NiCl_26H_2O$ | 0.000024 |
| $CuCl_2.2H_2O$ | 0.000017 |
| Biotin | 0.00001 |
| Folic acid | 0.00005 |
| Pyridoxine.HCl | 0.000025 |
| Riboflavin | 0.000025 |
| Nicotinic acid | 0.000025 |
| Pantothenic acid | 0.00025 |
| Vitamin $B_{12}$ | 0.000007 |
| P-Aminobenzoic acid | 0.00025 |

The following additions and or modifications were made to the PR basal medium for enrichments described above:

| Strain | Enrichment Nitrite (25 mM) | pH | Other |
|---|---|---|---|
| 5B-MGN-2P | (±)-2-methylglutaronitrile (Aldrich Chem. Co., Milwaukee, WI) | 7.2 | 30 disodium succinate/L |
| 3L-A-1-5-1a-1 3L-G-1-5-1a | (±)-2-methylglutaronitrile | 5.6 | 30 g glucose/L |
| 13-5S-ACN-2a | acetonitrile (Aldrich Chem. Co., Milwaukee, WI) | 7.2 | 30 g disodium succinate/L |

Strains were initially selected based on growth and ammonia production on the enrichment nitrile. Isolates were purified by repeated passing on Bacto Brain Heart Infusion Agar followed by screening for ammonia production from the enrichment nitrile.

Purified strains were identified based on membrane fatty acid analysis of the methyl esters following standard protocols (Mukawaya et al., J. Clin. Microbial, 1989, 27:2640–46) using the Microbial ID Software and Aerobe Library (Version 3.0) from Microbial ID Inc. (Newark, Del.) and standard bacteriological, physiological and biochemical tests enumerated below.

| | STRAIN | |
|---|---|---|
| CHARACTER | 13-5S-ACN-2a | 5B-MGN-2P |
| Gram Stain | Negative | Negative |
| Cell Morphology | Rod | Rod |
| Flagella | Lophotrichous | Lophotrichous |
| Pyocyanin | Negative | Negative |
| Pyoverdin | Positive | Positive |
| Argininedihydrolase | Positive | Positive |
| Growth at 41° C. | Negative | Negative |
| Gelatin Hydrolysis | Negative | Negative |
| Denitrification | Negative | Negative |
| Starch Hydrolysis | Negative | Negative |
| Use As Sole Carbon Source | | |
| Butylamine | Positive | Positive |
| Inositol | Positive | Negative |
| Citraconate | Positive | Negative |
| L-Tartrate | Negative | Positive |
| Genus species | *Pseudomonas putida* | *Pseudomonas putida* |

| | STRAIN | |
|---|---|---|
| Character | 3L-G-1-5-1a | 3L-A-1-5-1a-1 |
| Gram Stain | Negative | Negative |
| Cell Morphology | Rod | Coccoid Rod |
| Oxidase | Positive | Positive |
| Growth on Citrate | Positive | Positive |
| Urea Hydrolysis | Positive | Negative |
| Aerobic Oxidation of Dextrose | Positive | Negative |
| Aerobic Oxidation of Xylose | Positive | Negative |
| Indole Production | Negative | Negative |
| Hydrogen Sulfide Production | Negative | Negative |
| Nitrogen Production via Denitrification | Negative | Negative |
| Arginine Dihydroloase | Positive | Negative |
| Dextrose Fermentation | Negative | Negative |
| Motility | Not Tested | Negative |
| Genus species | Pseudomonas sp. | Group 4 Moraxella sp. |

For testing nitrile hydrolysis activity, PR basal medium with 10 g/L glucose was used to grow cell material. This medium was supplemented with 25 mM of (±)-2-methylglutaronitrile (5B-MGN-2P, 3L-G-1-5-1a) or 25 mM of 1,4-dicyanobutane (3L-A-1-5-1a-1, 13-5S-ACN-2a) or 25 mM of acetamide (all strains). *P. putida* 5B-MGN-2p was also grown in the absence of a nitrile or amide inducer with 25 mM of NH4Cl or (NH4)2SO4 replacing the nitrile or amide. A 10 mL volume of complete medium was inoculated with 0.1 mL of frozen stock culture (all strains). Following overnight growth at room temperature (22°–25° C.) on a shaker at 250 rpm, the 10 mL inoculum was added to 990 mL of fresh medium in a 2-L flask. The cells were grown overnight at room temperature with stirring at a rate high enough to cause bubble formation in the medium. Cells were harvested by centrifugation, washed once with 0.85% saline and the concentrated cell paste was immediately placed in a −70° C. freezer for storage. Thawed cell pastes containing approximately 80% water were used in all nitrile hydrolysis bioconversions.

The above stereospecific nitrile-hydrolyzing microorganisms were representative strains from a collection of microorganisms isolated via enrichment cultures described above. The stereospecific and stereoselective activities of nitrile-hydrolyzing microorganisms isolated from enrichment experiments are shown in Table 1.

minimum of experimentation to choose additional strains of Pseudomonas, Moraxella, and Serratia (and other genera as well) for converting all the nitrile starting reactants to their corresponding amides/acids.

Acid Hydrolysis of Chiral Amide to Chiral Acid

In the present invention, mineral acid can be used to hydrolyze the R- or S-amide derived from the R,S nitrile to the R- or S-acid. Interestingly, chiral cyanohydrins are hydrolyzed to the corresponding chiral hydroxy acids with concentrated mineral acid; see Effenberger, et al., Tetrahedron Letters, 1990, 31 (9): 1249–1252 and references cited therein. However, we have found that 2-aryl-2-alkyl acetonitriles are not hydrolyzed by mineral acid under conditions where the corresponding chiral amides are hydrolyzed to the chiral acids. The chiral acid can be easily separated from the undesired nitrile as described below.

In addition, a chiral amide can be hydrolyzed by an amidase enzyme such as the Brevibacterium and Corynebacterium strains described in EPA 326,482. This reaction does not require a stereospecific amidase and, therefore, any amidase which hydrolyzes racemic 2-aryl-alkylamides can be employed.

TABLE 1

STEREOSPECIFIC/STEREOSELECTIVE HYDROLYSIS WITH SOIL ENRICHMENT ISOLATES

| Microorganism[a] | Strain | Enrichment Nitrile[b] | CPIN R/S[c] | E[d] | NPCN[f] R/S[c] | E[d] | IBCN R/S[c] | E[d] |
|---|---|---|---|---|---|---|---|---|
| P. putida | 13-5S-ACN-2a | ACN | 90/10 | >10 | 0/100 | <7 | 10/90 | >10 |
| P. putida | 5B-MGN-2P | MGN | 77/33 | >10 | 43/57 | >7 | 30/70 | >10 |
| Pseudomonas sp. | 20-5-MGN-1P | MGN | No bioconversion | | 0/100 | <7 | No Bioconversion | |
| Moraxella sp. | 3L-A-1-5-1a-1 | MGN | 58/42 | >10 | 50/50 | <7 | 44/56 | >10 |
| Pseudomonas sp. | 3L-B-2-6-1P | ACN | No Bioconversion | | 59/41 | <7 | No Bioconversion | |
| Pseudomonas sp. | 3L-G-2-5-1a | ACN | 55/45 | >10 | 0/100 | <7 | 50/50 | >10 |
| Pseudomonas sp. | 20-5-SBN-1a | SBN | No Bioconversion | | No Bioconversion | | No Bioconversion | |
| Not Classified | 3L-G-1-2-1a | MGN | No Bioconversion | | 39/61 | >7 | No Bioconversion | |
| Pseudomonas sp. | 3L-G-1-5-1a | MGN | No Bioconversion | | 83/17 | 10 | No Bioconversion | |
| Pseudomonas sp. | 5A-MGN-1P | MGN | No Bioconversion | | NT[e] | NT[e] | No Bioconversion | |
| Pseudomonas sp. | 5B-ACN-1P | ACN | 58/42 | >10 | 47/53 | >10 | 49/51 | >10 |
| Pseudomonas sp. | 2G-8-5-1 | 4CP | No Bioconversion | | 92/8 | >10 | No Bioconversion | |
| P. auerofaciens | MOB C2-1 | PBN | 69/31 | >10 | 19/81 | >10 | 0/100 | >10 |
| S. liquefaciens | MOB IM/N3 | PPA | 54/48 | >10 | 21/79 | <7 | No Bioconversion | |
| Pseudomonas sp. | 2G-8-5-2 | 4CP | No Bioconversion | | 68/32 | <7 | No Bioconversion | |
| Pseudomonas | 2D-11-5-1 | NAN | 65/35 | >10 | 44/56 | >10 | 0/100 | >10 |
| P. putida[g] | 2D-11-5-1b | NAN | 69/31 | >10 | 17/83 | <7 | 0/100 | >10 |
| Pseudomonas sp.[g] | 2D-11-5-1c | NAN | No Bioconversion | | 100/0 | 8.8 | No Bioconversion | |
| Pseudomonas sp. | 20-5-SBN-1b | SBN | No Bioconversion | | NT[e] | <7 | 10/90 | >10 |

[a]Strain identification by fatty acid analysis as described in text.
[b]ACN = acetonitrile; MGN = 2-methylglutaronitrile; SBN = S-2-methylbutyronitrile; 4CP = 4-cyanophenol; NAN = 1-naphthoacetonitrile; PBN = phenylbutyronitrile; PPA = propionamide.
[c]Ratio of R-enantiomer to S-enantiomer remaining after 48–64 h incubation at 28° C.; determined by chiral HPLC.
[d]E = Enantiomer ratio as defined in text. Determined by reverse-phase HPLC and chiral HPLC.
[e]NT = not tested.
[f]Data corrected for trace of R,S-NPAm present in substrate.
[g]2D-11-5-1b and 2D-11-5-1c derived from 2D-11-5-1.

Microorganisms tend to undergo mutation. Thus, the bacteria, even if they are mutants of a competent strain listed above, can be used in the process according to the instant invention as long as its culture produces a stereospecific nitrile hydratase. Table 1, taken together with the disclosure presented herein, will enable one skilled in the art with a Step iii Racemization of Chiral Nitriles The combination of stereospecific microbial nitrile hydrolysis and mineral acid or amidase hydrolysis of amides yields a mixture of desired chiral acid and undesired chiral nitrile. Following separation of the undesired nitrile from the desired acid, e.g., by base neutralization and solvent extraction of the nitrile, recycling of the R- or S- nitrile requires racemization. We have found that chiral nitriles (in which $R^2$ is H) can be converted to racemic nitriles using a strongly basic ion exchange resin such as Amberlite® IRA-400 (OH) resin, Amberlyst® A-26, or Dowex® 1X8 resin (after exchange with hydroxide ion) in an organic solvent. This procedure results in high racemic nitrile yields with no substantial hydrolysis of the nitrile to the corresponding amide or acid. The resulting racemic nitrile can be hydrolyzed to the corresponding R- or S-acid under the conditions described previously.

Analytical Procedures

Nitriles and amide and acid products derived via microbial or mineral acid hydrolysis are measured by reverse-phase HPLC. Detection is by ultra-violet light absorbtion. A Du Pont Zorbax® C18 column employing a mobile phase of 70–75% methanol and 25–30% H2O acidified with 0.1% H3PO4 or 67% acetonitrile (ACN) and 33% H2O acidified with 0.1% H3PO4 is used. Chromatographic identity and quantitation of nitriles and their resulting amide and acid products can be determined by comparison with authentic standards.

Chiral HPLC for the separation of enantiomers can be carried out with an α1-acid glycoprotein column obtained from Chromtech (Sweden). The mobile phases for separation of various enantiomers is summarized below.

| Chiral HPLC Separation of Nitrile, Amide and Acid Enantiomers | |
|---|---|
| Enantiomers | Mobile Phase |
| CPIN, CPIAm, CPIA | 95% 0.01 M Phosphate Buffer (pH 6.0):5% Ethanol |
| NPCN, NPAm, NPAC | 95% 0.01 M Phosphate Buffer (pH 5.6):5% Ethanol |
| IBCN, IBAm, IBAC | 96% 0.02 M Phosphate Buffer (pH 5.2):4% Ethanol |

Enantiomeric composition, purity and chromatographic identity of the above nitriles, amides and acids were determined by comparison with authentic standard enantiomers or racemic mixtures.

GC analysis of CPIN, CPIAm and CPIA was carried out on a 183 cm×2 mm (i.d.) glass column containing 3% SP2100 on Supelco support (120 mesh). A temperature program starting at 125° C. for 5 minutes and 8° C. per minute to 250° C. was used.

The processes of this invention are illustrated by the following Examples.

EXAMPLE 1

Step i. A 100 mg (S-CPIN, R-CPIN hydrolysis) or 200 mg (R,S-CPIN hydrolysis) sample of frozen cell paste of *P. putida* 5B-MGN-2P was added to 3 mL of phosphate buffer (100 mM, pH7.0) at room temperature. Then, 30 to 40 μmol of S-CPIN or R-CPIN or R,S-CPIN in 120 μL of dimethyl sulfoxide was added. After incubation at 28° C. with agitation for 48 h, the reactions were acidified with 3M H2SO4 to pH 3.0. Four volumes of methylene chloride were added to each sample and the suspensions were agitated for 15–30 minutes. The methylene chloride layers were removed and evaporated to dryness under a stream of nitrogen and the residues were resuspended in 3 mL of methanol. The composition of the methanol solution was determined by reverse-phase HPLC and chiral HPLC and is shown in Table 2.

TABLE 2

S-CPIN, R-CPIN and R,S-CPIN Hydrolysis by *P. putida*, 5B-MGN-2P

| Substrate (μmol added) | HPLC Analysis (μmol recovered) | | | | | |
|---|---|---|---|---|---|---|
| | Reverse Phase | | Chiral | | | |
| | CPIN | CPIAm | S-CPIN | R-CPIN | S-CPIAm | R-CPIAm |
| S-CPIN (30.9) | 1.8 | 28.2 | 1.8 | ND[a] | 28.2 | ND[a] |
| R-CPIN (37.5) | 33.7 | 3.8 | NT[b] | NT[b] | NT[b] | NT[b] |
| R,S-CPIN (31.9) | 20.4 | 11.5 | 4.7 | 15.7 | 11.0 | 0.5 |

[a]ND = None Detected.
[b]NT = Not Tested.

EXAMPLE 2

Step i: A 50 mg sample of frozen cell paste of *P. putida* 5B-MGN-2p obtained from cultures propagated on PR glucose medium supplemented with 25 mM NH4Cl in place of 25 mM (±)-2-methylglutaronitrile was added to 1 mL of pyrophosphate buffer (5 mM, pH 7.5) at room temperature containing 20.6 μmole of S-CPIN or R,S-CPIN. After incubation at 28° C. with agitation for 24 h, the reaction was acidified with 3M H2SO4 to pH 3.0. Four volumes of methylene chloride were added to each sample and the suspensions were agitated for 15–30 min. The methylene chloride layers were removed and evaporated to dryness under a stream of nitrogen and the residues were resuspended in 1 mL of methanol. The composition of the methanol solution was determined by reverse-phase HPLC and chiral HPLC and is shown in Table 3.

TABLE 3

S-CPIN, R,S-CPIN Hydrolysis by *P. putida* 5B-MGN-2P
Propagated in the Absence of Nitrile or Amide Inducer

| Substrate | HPLC Analysis (μmol recovered) | | | | | |
|---|---|---|---|---|---|---|
| | Reverse Phase | | Chiral | | | |
| (μmol added) | CPIN | CPIAm | S-CPIN | R-CPIN | S-CPIAm | R-CPIAm |
| S-CPIN (20.6) | 1.2 | 17.7 | NT[a] | NT[a] | NT[a] | NT[a] |
| R,S-CPIN (20.6) | 15.1 | 3.3 | 6.0 | 9.1 | 3.3 | ND[b] |

[a]NT = Not Tested.
[b]ND = None Detected.

EXAMPLE 3

Step i. A 20 mg sample of frozen cell paste of *P. putida* 5B-MGN-2P was added to 1 mL of phosphate buffer (0.3 mM, pH 7.2) containing $MgCl_2 \cdot 6H_2O$ (2 mM) at room temperature. Then 0.95 μmol of R,S-NPCN in 40 μL of dimethyl sulfoxide was added. After incubation at 28° C. with agitation for 48 h, the reaction was acidified with 3M $H_2SO_4$ to pH 3.0. Four volumes of methylene chloride were added and the suspension was agitated for 30 min. The methylene chloride layer was removed and evaporated to dryness under a stream of nitrogen and the residue was resuspended in 1 mL of methanol. The composition of the extracted supernatant was determined by reverse-phase HPLC and chiral HPLC and is shown in Table 4.

TABLE 4

R,S-NPCN Hydrolysis by *P. putida* 5B-MGN-2P

| Substrate | HPLC Analysis (μmol recovered) | | | | | | | |
|---|---|---|---|---|---|---|---|---|
| | Reverse Phase[b] | | | Chiral[b] | | | | |
| (μmol added) | NPCN | NPAm | NPAC | S-NPCN | R-NPCN | S-NPAm | R-NPAm | S-NPAC |
| R,S-NPCN (0.95) | 0.5 | 0.22 | 0.03 | 0.28 | 0.22 | ND[a] | 0.22 | 0.03 |

[a]ND = None Detected.
[b]Data corrected for trace of R,S-NPAm present in substrate.

EXAMPLE 4

Step i. A 40 mg sample of frozen cell paste of *P. putida* 5B-MGN-2P was added to 1 mL of phosphate buffer (100 mM, pH 7.0) at room temperature. Then 10.7 μmol of R,S-IBCN in 40 μL of dimethylsulfoxide was added. After incubation at 28° C. with agitation for 48 h, the reaction was acidified with 3M $H_2SO_4$ to pH 3.0. Four volumes of methylene chloride were added and the suspension was agitated for 15–30 min. The methylene chloride layer was removed and evaporated to dryness under a stream of nitrogen and the residue was resuspended in 1 mL of methanol. The composition of the extracted supernatant is determined by reverse phase HPLC and chiral HPLC and is shown in Table 5.

TABLE 5

R,S-IBCN Hydrolysis by *P. putida* 5B-MGN-2P

| Substrate | HPLC Analysis (μmol recovered) | | | | | |
|---|---|---|---|---|---|---|
| | Reverse Phase | | Chiral | | | |
| (μmol added) | IBCN | IBAm | S-IBCN | R-IBCN | S-IBAm | R-IBAm |
| R,S-IBCN (10.7) | 7.9[a] | 2.8 | 5.5[a] | 2.4[a] | ND[b] | 2.8 |

[a]Estimated value calculated by substracting μmol IBAm recovered from μmol IBCN added.
[b]ND = None Detected.

EXAMPLE 5

Step i. A 50 mg sample of frozen cell paste of *Moraxella sp.* 3L-A-1-5-1a-1 was added to 1 mL of phosphate buffer (100 mM, pH 7.0) at room temperature. Then 10.3 μmol of S-CPIN, R-CPIN or R,S-CPIN in 40 μL of dimethyl sulfoxide was added. After incubation at 28° C. with agitation for 48 h, the reactions were acidified with 3M H2SO4 to pH 3.0. Four volumes of methylene chloride was added to each sample and the suspensions were agitated for 15–30 minutes. The methylene chloride layers were removed and evaporated to dryness under a stream of nitrogen and the residues were resuspended in 1 mL of methanol. The composition of the methanol solution was determined by reverse-phase HPLC and chiral HPLC and is shown in Table 6.

and extraction as in Example 3, the composition of the extracted supernatant was determined by reverse-phase HPLC and chiral HPLC. The results are shown in Table 8.

TABLE 6

S-CPIN, R-CPIN and R,S-CPIN Hydrolysis by Moraxella sp. 3L-A-1-5-1a-1

| | HPLC Analysis (μmol recovered) | | | | | |
|---|---|---|---|---|---|---|
| Substrate | Reverse Phase | | Chiral | | | |
| (μmol added) | CPIN | CPIAm | S-CPIN | R-CPIN | S-CPIAm | R-CPIAm |
| S-CPIN (10.3) | 0.5 | 8.7 | 0.5 | ND$^a$ | 8.7 | ND$^a$ |
| R-CPIN (10.3) | 10.3 | ND$^a$ | NT$^b$ | NT$^b$ | NT$^b$ | NT$^b$ |
| R,S-CPIN (10.3) | 9.7 | 0.5 | 4.1 | 5.6 | 0.5 | ND$^a$ |

$^a$ND = None Detected.
$^b$NT = Not Tested.

EXAMPLE 6

Step i. A 40 mg sample of frozen cell paste of *Moraxella sp.* 3L-A-1-5-1a-1 was added to 1 mL of phosphate buffer (100 mM, pH 7.0) at room temperature. In the same manner as in Example 4, 10.7 μmol of R,S-IBCN was added. Following the same incubation and extraction protocols as in Example 4, the composition of the extracted supernatant was determined by reverse-phase and chiral HPLC. The results are shown in Table 7.

TABLE 7

R,S-IBCN Hydrolysis by Moraxella sp. 3L-A-1-5-1a-1

| | HPLC Analysis (μmol recovered) | | | | | | | | |
|---|---|---|---|---|---|---|---|---|---|
| Substrate | Reverse Phase | | | Chiral | | | | | |
| (μmol added) | IBCN | IBAm | IBAC | S-IBCN | R-IBCN | S-IBAm | R-IBAm | S-IBAC | R-IBAC |
| R,S-IBCN (10.7) | 9.8$^a$ | 0.4 | 0.5 | 5.5$^a$ | 4.3$^a$ | ND$^b$ | 0.4 | ND$^b$ | 0.5 |

$^a$Estimated value calculated by substracting μmol amide recovered from μmol IBCN added.
$^b$ND = None Detected.

EXAMPLE 7

Step i. A 20 mg sample of frozen cell paste of *Pseudomonas sp.* 3L-G- 1-5-1a, was added to phosphate buffer (0.3 mM, pH 7.0) containing MgCl2.6H2O (2 mM) at room temperature. In the same manner as in Example 3, 0.95 μmol of R,S-NPCN was added. Following the same incubation

TABLE 8

R,S-NPCN Hydolysis by Pseudomonas sp. 3L-G-1-5-1a

| Substrate | Reverse Phase[b] | | | Chiral[b] | | | | |
|---|---|---|---|---|---|---|---|---|
| (μmol added) | NPCN | NPAm | NPAC | S-NPCN | R-NPCN | S-NPAm | R-NPAm | S-NPAC |
| R,S-NPCN (0.95) | 0.44 | 0.3 | 0.30 | 0.03 | 0.41 | ND[a] | 0.03 | 0.30 |

[a]ND = None Detected.
[b]Data corrected for trace of R,S-NPAm present in substrate.

EXAMPLE 8

Step i. A 100 mg sample of frozen cell paste of *P. putida* 13-5S-ACN-2a was added to 3 mL of phosphate buffer (100 mM, pH 7.0) at room temperature. In the same manner as in Example 1, 30.9 μmol of S-CPIN, R-CPIN or R,S-CPIN was added. Following the same incubation and extraction protocols as in Example 1, the composition of the extracted supernatants was determined by reverse-phase HPLC and chiral HPLC. The results are shown in Table 9.

Example 5, 10.3 μmol of S-CPIN or R,S-CPIN was added. Following the same incubation and extraction protocols as in Example 5, the composition of the extracted supernatants was determined by reverse-phase HPLC and chiral HPLC. The results are shown in Table 11.

TABLE 9

**S-CPIN, R-CPIN, R,S-CPIN Hydrolysis by *P. putida* 13-5S-ACN-2a**

| Substrate | Reverse Phase | | Chiral | | | |
|---|---|---|---|---|---|---|
| (μmol added) | CPIN | CPIAm | S-CPIN | R-CPIN | S-CPIAm | R-CPIAm |
| S-CPIN (30.9) | ND[a] | 30.2 | ND[a] | ND[a] | 30.2 | ND[a] |
| R-CPIN (30.9) | 28.5 | 0.6 | NT[b] | NT[b] | NT[b] | NT[b] |
| R,S-CPIN (30.9) | 13.2 | 14.7 | 1.3 | 11.9 | 14.0 | 0.7 |

[a]ND = None Detected.
[b]NT = Not Tested.

EXAMPLE 9

Step i. A 40 mg example of frozen cell paste of *P. putida* 13-5S-ACN-2a was added to phosphate buffer (100 mM, pH 7.0) at room temperature. In the same manner as in Example 4, 10.7 μmol of R,S-IBCN was added. Following the same incubation and extraction protocols as in Example 4, the composition of the extracted supernatant was determined by reverse-phase HPLC and chiral HPLC. The results are shown in Table 10.

TABLE 10

**R,S-IBCN Hydrolysis by *P. putida* 13-5S-ACN-2a**

| Substrate | Reverse Phase | | Chiral | | | |
|---|---|---|---|---|---|---|
| (μmol added) | IBCN | IBAm | S-IBCN | R-IBCN | S-IBAm | R-IBAm |
| R,S-IBCN (10.7) | 6.6[a] | 4.1 | 5.9[a] | 0.7[a] | ND[b] | 4.1 |

[a]Estimated value calculated by substracting μmol IBAm recovered from μmol IBCN added.
[b]ND = None Detected.

EXAMPLE 10

Step i. A 50 mg sample of frozen cell paste of *P. putida* 2D-11-5-1b was added to 1 mL of phosphate buffer (100 mM, pH 7.0) at room temperature. In the same manner as

TABLE 11

**S-CPIN, R,S-CPIN Hydrolysis by *P. putida* 2D-11-5-1b**

| Substrate | HPLC Analysis (μmol recovered) | | | | | |
|---|---|---|---|---|---|---|
| | Reverse Phase | | Chiral | | | |
| (μmol added) | CPIN | CPIAm | S-CPIN | R-CPIN | S-CPIAm | R-CPIAm |
| S-CPIN (10.3) | ND | 10.0 | ND | ND | 10.0 | ND |
| R,S-CPIN (10.3) | 8.5 | 3.0 | 2.6 | 5.9 | 3.0 | ND |

ND = None Detected.
Apparent excess recovery of CPIN was most likely due to experimental error.

EXAMPLE 11

Step i. A 50 mg sample of frozen cell paste of *P. putida* 2D-11-5-1b was added to 2 mL of phosphate buffer (100 mM, pH 7.0) at room temperature. In the same manner as in Example 4, 10.7 μmol of R,S-IBCN was added. Following the same incubation and extraction protocols as in Example 4, the composition of the extracted supernatant was determined by reverse-phase HPLC and chiral HPLC. The results are shown in Table 12.

TABLE 12

**R,S-IBCN Hydrolysis by *P. putida* 2D-11-5-1b**

| Substrate | HPLC Analysis (μmol recovered) | | | | | |
|---|---|---|---|---|---|---|
| | Reverse Phase | | Chiral | | | |
| (μmol added) | IBCN | IBAm | S-IBCN | R-IBCN | S-IBAm | R-IBAm |
| R,S-IBCN (10.7) | 7.1[a] | 3.6 | 5.0[a] | 2.1[a] | 0.4 | 3.2 |

[a]Estimated value calculated by substracting μmol IBAm recovered from μmol IBCN added.

EXAMPLE 12

Step i. A 50 mg sample of frozen cell paste of *S. liquefaciens* MOB IM/N3 was added to 1 mL of phosphate buffer (100 mM, pH 7.0) at room temperature. In the same manner as Example 5, 10.3 μmol of S-CPIN, R-CPIN or R,S-CPIN was added. Following the same incubation and extraction protocols as in Example 5, the composition of the extracted supernatants was determined by reverse-phase HPLC and chiral HPLC. The results are shown in Table 13.

TABLE 13

**S-CPIN, R-CPIN Hydrolysis by *S. liquefactions* MOB IM/N3**

| Substrate | HPLC Analysis (μmol recovered) | | | | | |
|---|---|---|---|---|---|---|
| | Reverse Phase | | Chiral | | | |
| (μmol added) | CPIN | CPIAm | S-CPIN | R-CPIN | S-CPIAm | R-CPIAm |
| S-CPIN (10.3) | 0.8 | 8.2 | NT[a] | NT[a] | NT[a] | NT[a] |
| R-CPIN (10.3) | 9.5 | <0.1 | NT[a] | NT[a] | NT[a] | NT[a] |
| R,S-CPIN (10.3) | 8.6 | 1.2 | 4.0 | 4.6 | 1.2 | ND[b] |

[a]NT = Not Tested.
[b]ND = None Detected.

EXAMPLE 13

Step i. A 50 mg sample of frozen cell paste of *P. aureofaciens* MOB C2-1 was added to 1 mL of phosphate buffer (100 mM, pH 7.0) at room temperature. In the same manner as Example 5, 10.3 μmol of S-CPIN, R-CPIN or R,S-CPIN was added. Following the same incubation and extraction protocols as in Example 5, the composition of the extracted supernatants was determined by reverse-phase HPLC and chiral HPLC. The results are shown in Table 14.

TABLE 14

S-CPIN, R-CPIN, R,S-CPIN Hydrolysis by *P. aureofaciens* MOB C2-1

| Substrate | HPLC Analysis (μmol recovered) | | | | | |
|---|---|---|---|---|---|---|
| | Reverse Phase | | Chiral | | | |
| (μmol added) | CPIN | CPIAm | S-CPIN | R-CPIN | S-CPIAm | R-CPIAm |
| S-CPIN (10.3) | ND[a] | 8.4 | ND[a] | ND[a] | 8.4 | ND[a] |
| R,CPIN (10.3) | 9.0 | <1.0 | NT[b] | NT[b] | NT[b] | NT[b] |
| R,S-CPIN (10.3) | 8.4 | 1.0 | 2.6 | 5.8 | 1.0 | ND[a] |

[a]ND = None Detected.
[b]NT = Not Tested.

EXAMPLE 14

Step i. A 50 mg sample of frozen cell paste of *P. aureofaciens* MOB C2-1 was added to 1 mL of phosphate buffer (100 mM, pH 7.0) at room temperature. In the same manner as in Example 4, 10.7 μmol of R,S-IBCN was added. Following the same incubation and extraction protocols as in Example 4, the composition of the extracted supernatant was determined by reverse-phase HPLC and chiral HPLC. The results are shown in Table 15.

TABLE 15

R,S-IBCN Hydrolysis by *P. aureofaciens* MOB C2-1

| Substrate | HPLC Analysis (μmol recovered) | | | | | |
|---|---|---|---|---|---|---|
| | Reverse Phase | | Chiral | | | |
| (μmol added) | IBCN | IBAm | S-IBCN | R-IBCN | S-IBAm | R-IBAm |
| R,S-IBCN (10.7) | 8.3[a] | 2.4 | 5.4[a] | 2.9[a] | ND[b] | 2.4 |

[a]Estimated value calculated by substracting μmol IBAm recovered from μmol IBCN added.
[b]None Detected.

EXAMPLE 15

Step i. Approximately 20 mg of frozen cell paste of *Pseudomonas sp.*, 2G-8-5-1a, was added to 1 mL of phosphate buffer (0.1M, pH 7.2) at room temperature. Then approximately 1 μmol of R,S-NPCN in 40 μL of dimethyl sulfoxide was added. After incubation at 28° C. with agitation for 48 h, the reaction was acidified to pH 3.0 with 3M H2SO4. Four volumes of methylene chloride were added and the suspension was agitated for 30 min. The methylene chloride layer was removed and evaporated to dryness under a stream of nitrogen. The residue was redissolved in 1 mL of methanol. The composition of the extracted supernatant was determined by reverse-phase HPLC and chiral HPLC as described elsewhere. The results are shown in Table 16.

EXAMPLE 16

Step i. Approximately 10 mg of frozen cell paste of *Pseudomonas sp.*, 2D-11-5-1c, was added to 1 mL of phosphate buffer (0.1M, pH 7.2) at room temperature. Then approximately 1 μmol of R,S-NPCN in 40 μL of dimethyl sulfoxide was added. After incubation at 28° C. with agitation for 48 h, the reaction was acidified to pH 3.0 with 3M H2SO4. Four volumes of methylene chloride were added and the suspension was agitated for 30 min. The methylene chloride layer was removed and evaporated to dryness under a stream of nitrogen. The residue was redissolved in 1 mL of methanol. The composition of the extracted supernatant was determined by reverse-phase HPLC and chiral HPLC as described elsewhere. The results are shown in Table 17.

TABLE 16

R,S-NPCN hydrolysis by Pseudomonas sp., 2G-8-5-1a

| Substrate | HPLC Analysis (μmol recovered) | | | | | | | | |
|---|---|---|---|---|---|---|---|---|---|
| | Reverse Phase[b] | | | Chiral[b] | | | | | |
| (μmol added) | NPCN | NPAm | NPAc | S-NPCN | R-NPCN | S-NPAm | R-NPAm | S-NPAc | R-NPAc |
| R,S-NPCN (0.95) | 0.52 | 0.04 | 0.36 | ND[a] | 0.52 | ND | 0.04 | 0.36 | ND |

[a]ND = None Detected.
[b]Data corrected for trace of R,S-NPAm present in substrate.

TABLE 17

R,S-NPCN hydrolysis by Pseudomonas sp., 2D-11-5-1c

| Substrate | Reverse Phase[b] | | | Chiral[b] | | | | | |
|---|---|---|---|---|---|---|---|---|---|
| (μmol added) | NPCN | NPAm | NPAc | S-NPCN | R-NPCN | S-NPAm | R-NPAm | S-NPAc | R-NPAc |
| R,S-NPCN (0.95) | 0.66 | 0.09 | 0.40 | ND[a] | 0.66 | 0.04 | 0.05 | 0.4 | ND |

[a]ND = None Detected.
[b]Data corrected for trace of R,S-NPAm present in substrate.

EXAMPLE 17

Step i. Approximately 2 mg of frozen cell paste of *P. aureofaciens*, MOB C2-1, was added to 1 mL of phosphate buffer (0.1M, pH 7.2) at room temperature. Then approximately 1 μmol of R,S-NPCN in 40 μL of dimethyl sulfoxide was added. After incubation at 28° C. with agitation for 48 h, the reaction was acidified to pH 3.0 with 3M H2SO4. Four volumes of methylene chloride were added and the suspension was agitated for 30 min. The methylene chloride layer was removed and evaporated to dryness under a stream of nitrogen. The residue was redissolved in 1 mL of methanol. The composition of the extracted supernatant was determined by reverse-phase HPLC and chiral HPLC as described elsewhere. The results are shown in Table 18.

TABLE 18

R,S-NPCN hydrolysis by P. aureofaciens, MOB C2-1

| Substrate | Reverse Phase[b] | | | Chiral[b] | | | | | |
|---|---|---|---|---|---|---|---|---|---|
| (μmol added) | NPCN | NPAm | NPAc | S-NPCN | R-NPCN | S-NPAm | R-NPAm | S-NPAc | R-NPAc |
| R,S-NPCN (0.95) | 0.66 | 0.17 | ND | 0.53 | 0.13 | ND | 0.17 | ND | ND |

[a]ND = None Detected.
[b]Data corrected for trace of R,S-NPAm present in substrate.

EXAMPLE 18

Step ii. A suspension of 1.00 g of S-CPIAm in 16 mL of aqueous hydrochloric acid (18%) was stirred and heated to reflux. As the suspension was heated, the solid dissolved. After 16 h, the reaction mixture was cooled. The solid which precipitated and solidified around the stirrer was extracted with methylene chloride. Evaporation of the extract left 0.98 g of colorless solid which was analyzed by a combination of GC and HPLC. It was shown by GC to be mainly CPIA (92.3 area percent) with the remainder being unchanged amide. The configuration of the acid was established, by chiral HPLC as being the S-enantiomer (at least 98.2%), with only a trace of the reacemized R-enantiomer.

EXAMPLE 19

Step ii. The reaction was repeated as in Example 18 using 1.02 g of S-CPIAm and 15 mL of concentrated hydrochloric acid. After approximately 16 h at reflux, the reaction mixture was cooled and the precipitated solid was collected by filtration and air dried. There was recovered 0.96 g of colorless solid which was characterized by GC/mass spectrometry and by HPLC. The major component was identified as CPIA (96%) with about 4% of unchanged amide. Chiral HPLC showed that the acid was 96.6% of the S-enantiomer and 3.4% of the R-enantiomer.

EXAMPLE 20

Step iii. One g of wet Amberlite® IRA-400 (OH⁻ form) was treated with 10 mL of 5% NaOH for 10 min with stirring, filtered and washed with distilled water until the washings were neutral. The solid was suspended in 25 mL of absolute ethanol and 1.06 g of R-CPIN was added. This was stirred and heated to reflux for 64 h. After removal of the resin by filtration, the filtrate was cooled and rotary-evaporated to leave 1.01 g of colorless oil. Chiral HPLC analysis showed the oil to be a 50/50 mixture of R- and S-CPIN.

A method that shows the relative stability of R,S alkyl nitriles such as CPIN and their lack of conversion to the corresponding acids under relatively strong reaction conditions is as follows. A suspension of 9.70 g of R,S-CPIN in 100 mL of concentrated hydrochloric acid was heated to reflux for 16 h. The reaction mixture was cooled and extracted three times with methylene chloride. The combined extracts were washed with water and dried over anhydrous magnesium sulfate. Removal of the solvent left a colorless oil which was characterized by GC. There was a single main component (over 90%) with the same retention time as authentic starting nitrile. There was no evidence for the corresponding acid which would be produced by hydrolysis.

What is claimed is:

1. A method for converting a nitrile in an R, S mixture of nitriles of the formula

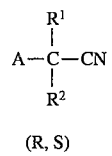

I (R, S)

wherein:

A is selected from the group consisting of:

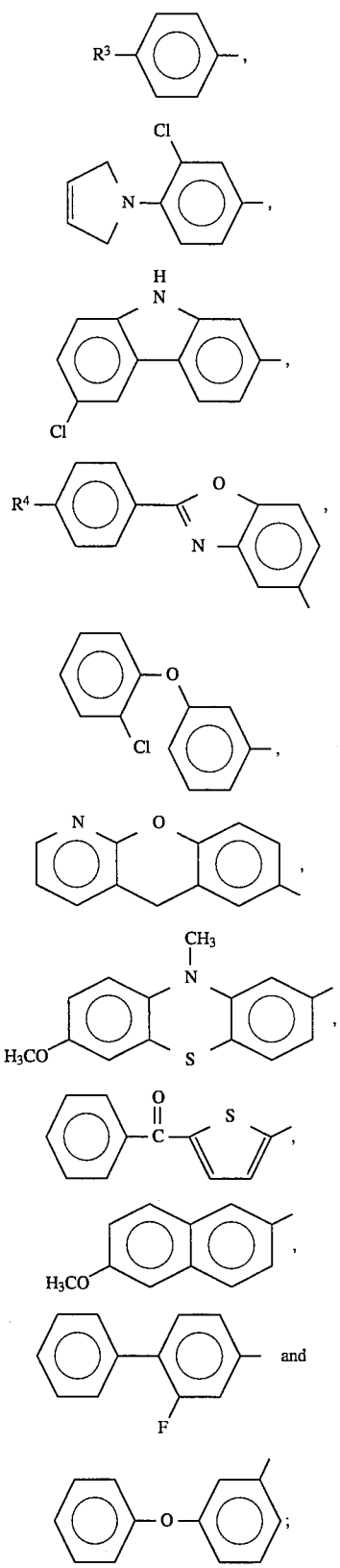

A-1
A-2
A-3
A-4
A-5
A-6
A-7
A-8
A-9
A-10
A-11

$R^1$ is $C_1$–$C_4$ alkyl;
$R^2$ is H or OH;
$R^3$ is H, Cl, $OCF_2H$, $(CH_3)_2CHCH_2$, $H_2C=C(CH_3)CH_2NH$,

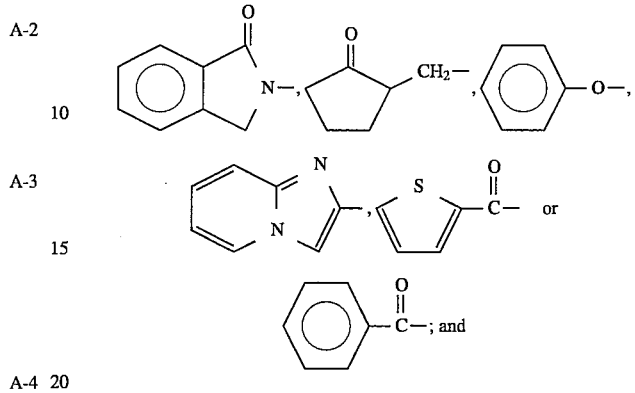

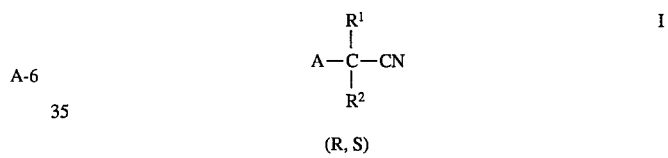

$R^4$ is Cl or F;
to the corresponding amide comprising contacting said nitrile mixture with a biological material that stereospecifically converts the R- or S-nitrile in said mixture to the corresponding enantiomeric R or S-amide, the biological material being located in or obtained from *Pseudomonas putida*, *Pseudomonas aureofaciens* or *Serratia liquefaciens*.

2. A method for converting a nitrile in an R, S mixture of nitriles of the formula $$A-\underset{R^2}{\overset{R^1}{\underset{|}{\overset{|}{C}}}}-CN \qquad I$$

(R, S)

wherein:
A is selected from the group consisting of:

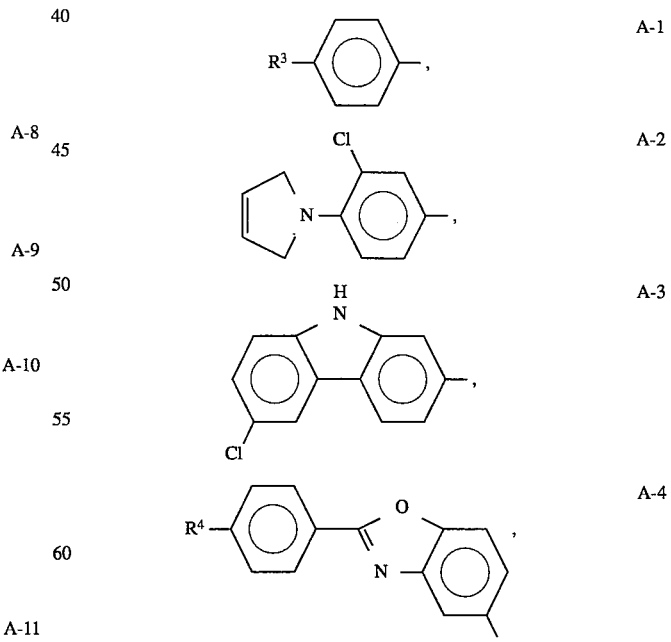

A-1
A-2
A-3
A-4

27
-continued

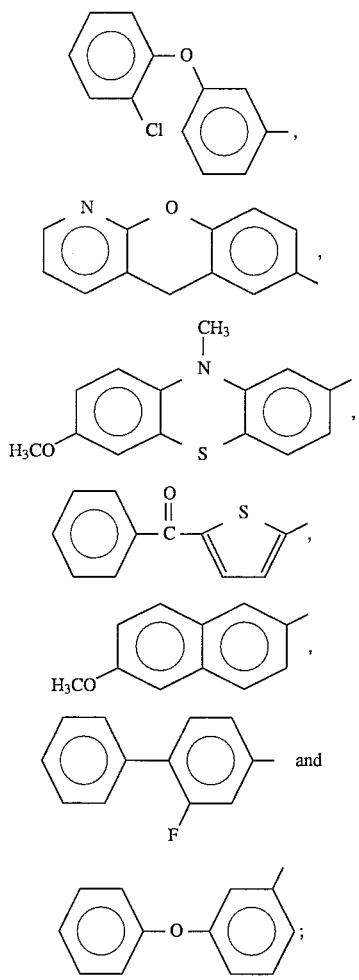

R¹ is C₁–C₄ alkyl;
R² is H or OH;
R³ is H, Cl, OCF₂H, (CH₃)₂CHCH₂, H₂C=C(CH₃)CH₂NH,

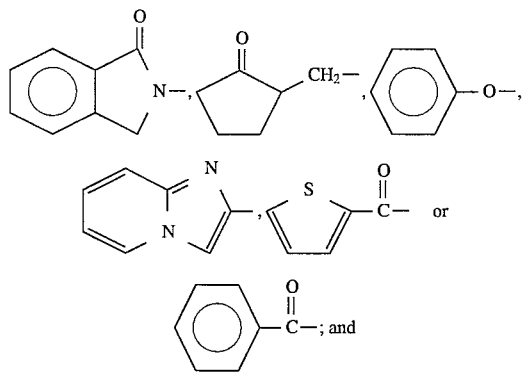

R⁴ is Cl or F;
to the corresponding amide comprising contacting said nitrile mixture with a biological material that stereospecifically converts the R- or S-nitrile in said mixture to the corresponding enantiomeric R or S-amide, the biological material being located in or obtained from *Pseudomonas putida* 13-5S-ACN-2a, *Pseudomonas putida* 5B-MGN-2P, 28
*Pseudomonas putida* 2D-11-5-1b, *Pseudomonas sp.* 20-5-MGN-1P, *Pseudomonas sp.* 3L-B-2-6-1P, *Pseudomonas sp.* 3L-G-2-5-1a, *Pseudomonas sp.* 3L-G-1-5-1a, *Pseudomonas sp.* 5A-MGN-1P, *Pseudomonas sp.* 5B-ACN-1P, *Pseudomonas sp.* 2G-8-5-2, *Pseudomonas sp.* 2G-8-5-1, *Pseudomonas sp.* 2D-11-5-1, Pseudomonas sp. 2D-11-5-1c, *Pseudomonas sp.* 20-5-SBN-1b, *Pseudomonas aureofaciens* MOB C2-1, *Moraxella sp.* 3L-A-1-5-1a-1, *Serratia liquefaciens* MOB IM/N3 or strain 3L-G-1-2-1a.

3. The method according to claim 1 or 2 wherein A is selected from the group

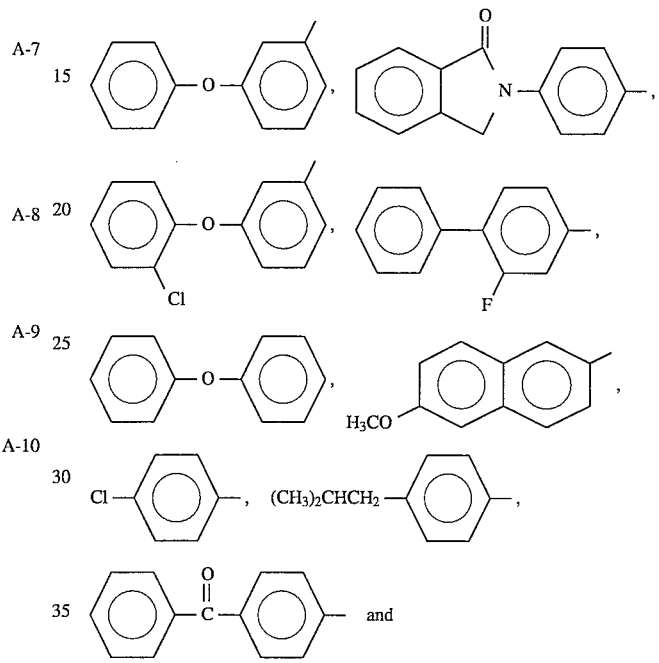

R¹ is selected from CH₃ and CH(CH₃)₂.

4. The method according to claim 2 wherein A is selected from the group

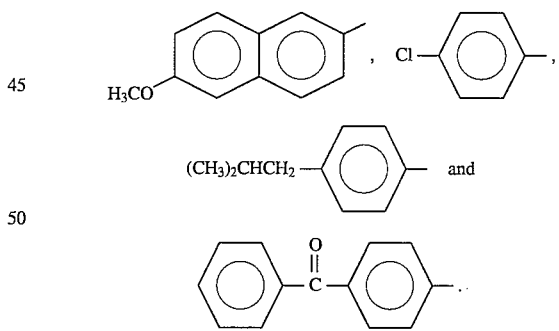

5. The method according to claim 4 wherein the nitrile is selected from the group (2-(4-chlorophenyl)-3-methylbutyronitrile, 2-(4-isobutylphenyl)propionitrile and 2-(6-methoxy-2-naphthyl)-propionitrile.

6. The method according to claim 5 wherein the nitrile is selected from the group 2-(4-chlorophenyl)-3-methylbutyronitrile and 2-(6-methoxy-2-naphthyl)propionitrile.

7. The method of claim 1 wherein the biological material is located in or obtained from *Pseudomonas putida* or *Serratia liquefaciens*.

8. The method according to claim 7 wherein the biological material is located in or obtained from *Pseudomonas putida*.

9. The method according to claim 8 wherein the biological material is located in or obtained from *Moraxella sp* 3L-A-1-5-1A-1.

10. The method according to claim 7 wherein the bio logical material is located in or obtained from *Serratia liquefaciens*.

* * * * *

UNITED STATES PATENT AND TRADEMARK OFFICE
CERTIFICATE OF CORRECTION

PATENT NO. : 5,593,871
DATED : January 14, 1997
INVENTOR(S) : Anton et al.

It is certified that error appears in the above-identified patent and that said Letters Patent is hereby corrected as shown below:

At the bottom of column 7, the 1st line of text in the table, after 7.2 30 insert "g". The corrected text should read "7.2 30 g disodium succinate/L."

Signed and Sealed this

Tenth Day of February, 1998

*Attest:*

BRUCE LEHMAN

*Attesting Officer*  Commissioner of Patents and Trademarks